US009605165B2

(12) United States Patent
Bastioli et al.

(10) Patent No.: US 9,605,165 B2
(45) Date of Patent: Mar. 28, 2017

(54) COMPLEX OLIGOMERIC STRUCTURES

(71) Applicant: Novamont S.p.A., Novara (IT)

(72) Inventors: Catia Bastioli, Novara (IT); Luigi Capuzzi, Novara (IT); Paolo Magistrali, Novara (IT); Sebastià Gesti' Garcia, Turin (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 14/957,804

(22) Filed: Dec. 3, 2015

(65) Prior Publication Data

US 2016/0152844 A1  Jun. 2, 2016

Related U.S. Application Data

(63) Continuation of application No. 13/995,735, filed as application No. PCT/EP2011/073492 on Dec. 20, 2011, now Pat. No. 9,212,124.

(30) Foreign Application Priority Data

Dec. 20, 2010  (IT) .............................. MI2010A2324

(51) Int. Cl.
| | |
|---|---|
| *C09D 11/00* | (2014.01) |
| *C08G 63/12* | (2006.01) |
| *C08K 5/10* | (2006.01) |
| *C08L 9/06* | (2006.01) |
| *C08L 21/00* | (2006.01) |
| *C08K 5/103* | (2006.01) |
| *C07C 67/293* | (2006.01) |
| *C08L 67/00* | (2006.01) |

(52) U.S. Cl.
CPC ............ *C09D 11/00* (2013.01); *C07C 67/293* (2013.01); *C08G 63/12* (2013.01); *C08K 5/10* (2013.01); *C08K 5/103* (2013.01); *C08L 9/06* (2013.01); *C08L 21/00* (2013.01); *C08L 67/00* (2013.01)

(58) Field of Classification Search
CPC . C11C 3/10; C11C 3/003; C07C 67/03; Y02E 50/13; C10L 1/026; C09D 11/00
USPC ............................... 554/169, 227; 106/31.13
See application file for complete search history.

(56) References Cited

U.S. PATENT DOCUMENTS

| | | |
|---|---|---|
| 1,815,886 A | 7/1931 | Herman |
| 5,717,022 A | 2/1998 | Beckmann et al. |
| 6,562,939 B1 | 5/2003 | Farachi et al. |

FOREIGN PATENT DOCUMENTS

| | | |
|---|---|---|
| EP | 0761734 A1 | 3/1997 |
| WO | WO-0055236 A1 | 9/2000 |

*Primary Examiner* — Deborah D Carr
(74) *Attorney, Agent, or Firm* — Polsinelli PC

(57) ABSTRACT

Mixture of triglycerides obtained from vegetable oils comprising one or more of the following oligomeric structures:

R4-[O—C(O)—R1-C(O)—O—CH2-CH(OR2)-CH2]$_n$-O—R3 wherein
R1 is selected from C2-C22 alkylenes,
R2 is selected from one or more of the following groups consisting of C6-C24 dicarboxylic acid residues and C6-C24 monocarboxylic acid residues,
R3 is selected from one or more of the following groups consisting of H, C6-C24 dicarboxylic acid residues and C6-C24 monocarboxylic acid residues,
R4 is an alkyl group,
n is an integer greater than or equal to 2,
said C6-C24 dicarboxylic acid residues of R2 and R3 being esterified with monoalcohols and said mixture of triglycerides having a Numerical Average Molecular Weight (Mn) of between 800 and 10.000 Da.

16 Claims, 3 Drawing Sheets

H-NMR SPECTRUM

COMPLEX OLIGOMERIC STRUCTURES

CROSS REFERENCE TO RELATED APPLICATIONS

This application is a Continuation of application Ser. No. 13/995,735 filed on Jun. 19, 2013, which is a National Phase filing under 35 U.S.C. §371 of PCT/EP2011/073492 filed on Dec. 20, 2011; and this application claims priority to Application No. MI2010A002324 filed in Italy on Dec. 20, 2010 under 35 U.S.C. §119. The entire contents of these applications are hereby incorporated by reference.

This invention relates to complex oligomeric structures obtained from vegetable oils, particularly to a mixture of oligomeric triglycerides containing esterified acid groups, the said structures being characterised by high stability to hydrolysis and thermooxidation, as well as having high viscosity. These structures can be used as extender oils or additives for rubbers, low pour point high stability lubricants, plasticisers for conventional plastics and bioplastics, polyurethane components, detergent components and bleaching agents, ink components, and monomer units in thermoplastic and thermosetting polymers.

The prospect of increasingly more restricted availability of materials of fossil origin in nature such as petroleum now make it urgent to replace its derivatives with other compounds of natural origin. The requirement to use raw materials from renewable sources to ensure the eco-sustainability of industrial outputs is particularly apparent in the production of consumables, especially in the sectors of plastics, rubber and lubricants.

As far as the plastics industry is concerned, for example, bioplastics in which conventional monomers derived from oil are replaced by raw materials from renewable sources are being developed. With a view to increasing environmental sustainability it is necessary when replacing monomers to look towards increasingly more thorough conversion of present polymer formulations, including the additives used for their processing.

In the field of elastomers it is common practice to use extender oils having a plasticising action derived from the processing of oil to extend the volume of rubbers and thus reduce production costs. The use of these extender oils of mineral origin has disadvantages associated with the high toxicity and carcinogenicity of their components, such as polycyclic aromatic hydrocarbons (PAH).

Even as far as lubricants are concerned, there has long been an increasingly stringent need to replace mineral lubricants with lubricants of renewable origin.

This invention identifies products of natural origin which are alternatives to those of fossil origin, do not have the disadvantages described above and are at the same time able to provide functional properties substantially similar to those of conventional products of non-renewable origin.

In particular, the object of this invention is a mixture of triglycerides obtained from vegetable oils comprising one or more of the following oligomeric structures:

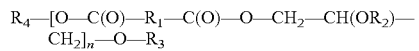

wherein $R_1$ is selected from $C_2$-$C_{22}$ alkylenes, $R_2$ is selected from one or more of the following groups consisting of $C_6$-$C_{24}$ dicarboxylic acid residues and $C_6$-$C_{24}$ monocarboxylic acid residues, $R_3$ is selected from one or more of the following groups consisting of H, $C_6$-$C_{24}$ dicarboxylic acid residues and $C_6$-$C_{24}$ monocarboxylic acid residues, $R_4$ is an alkyl group, n is an integer greater than or equal to 2, said $C_6$-$C_{24}$ dicarboxylic acid residues of R2 and R3 being esterified with monoalcohols and said mixture of triglycerides having a Numerical Average Molecular Weight (Mn) of between 800 and 10.000 Da.

With reference to the structure above, it is preferred that $R_1$ is a $C_6$-$C_{11}$ alkylene, $C_6$, —$C_7$ and/or $C_{11}$ alkylene being particularly preferred. The two or more $R_1$ in the structure can be different from each other.

$R_2$ represents $C_6$-$C_{24}$ dicarboxylic acid residues or $C_6$-$C_{24}$ monocarboxylic acid residues or a mixture thereof. The two or more $R_2$ in the structure can be different from each other.

$R_3$ represents a $C_6$-$C_{24}$ dicarboxylic acid residue or a $C_6$-$C_{24}$ monocarboxylic acid residue.

When $R_2$ and/or $R_3$ represents $C_6$-$C_{24}$ dicarboxylic acid residues, the free acid groups of $C_6$-$C_{24}$ dicarboxylic acid residues are esterified with linear or branched $C_1$-$C_{12}$ monoalcohols. Short chain monoalcohols such as for example methyl alcohol, ethyl alcohol, propyl alcohol and butyl alcohol are particularly preferred. Ethyl alcohol and butyl alcohol are particularly advantageous.

$R_4$ is preferably a linear or branched $C_1$-$C_{12}$ alkyl group, more preferably a $C_2$ or a $C_4$ alkyl group.

By $C_6$-$C_{24}$ dicarboxylic acids are meant aliphatic diacids, preferably of the alpha-omega type. Suberic acid, azelaic acid and brassylic acids and their mixtures are particularly preferred.

By $C_6$-$C_{24}$ monocarboxylic acid are meant monoacids possibly having one or more unsaturations along the chain and being unsubstituted or substituted.

Preferred unsubstituted monocarboxylic acids are mono acids having a chain length of $C_{9\text{-}24}$, palmitic, stearic, oleic, arachic, behenic and lignoceric acids being particularly preferred.

With reference to substituted monocarboxylic acids, long chain monocarboxylic acids with one or more keto groups or hydroxyl groups in a non-terminal position are preferred, among these $C_{12}$-$C_{24}$ carboxylic acids containing at least a ketone group or $C_{12}$-$C_{24}$ hydroxy acids containing at least one secondary hydroxyl group are particularly preferred. Examples of preferred substituted monocarboxylic acids are 9-hydroxystearic acid, 9-ketostearic acid, 10-ketostearic acid and 10-hydroxystearic acid.

Said substituted monocarboxylic acids may have two adjacent hydroxyl groups or an hydroxyl group adjacent to a keto group. If two adjacent hydroxyl groups are present, dihydroxypalmitic, dihydroxystearic, dihydroxyoleic, dihydroxyarachic and dihydroxybehenic acids are preferred. 9,10-dihydroxystearic acid is particularly preferred.

Advantageously, the oligomeric structures according to the invention are dimer or trimer esters of triglycerides having a number of repeating units (n) equal to 2 or equal to 3. Particularly preferred are dimer and trimer esters of triglycerides containing $C_6$-$C_{24}$ dicarboxylic acid residues. Example of preferred dimer and trimer esters are represented by the following structures:

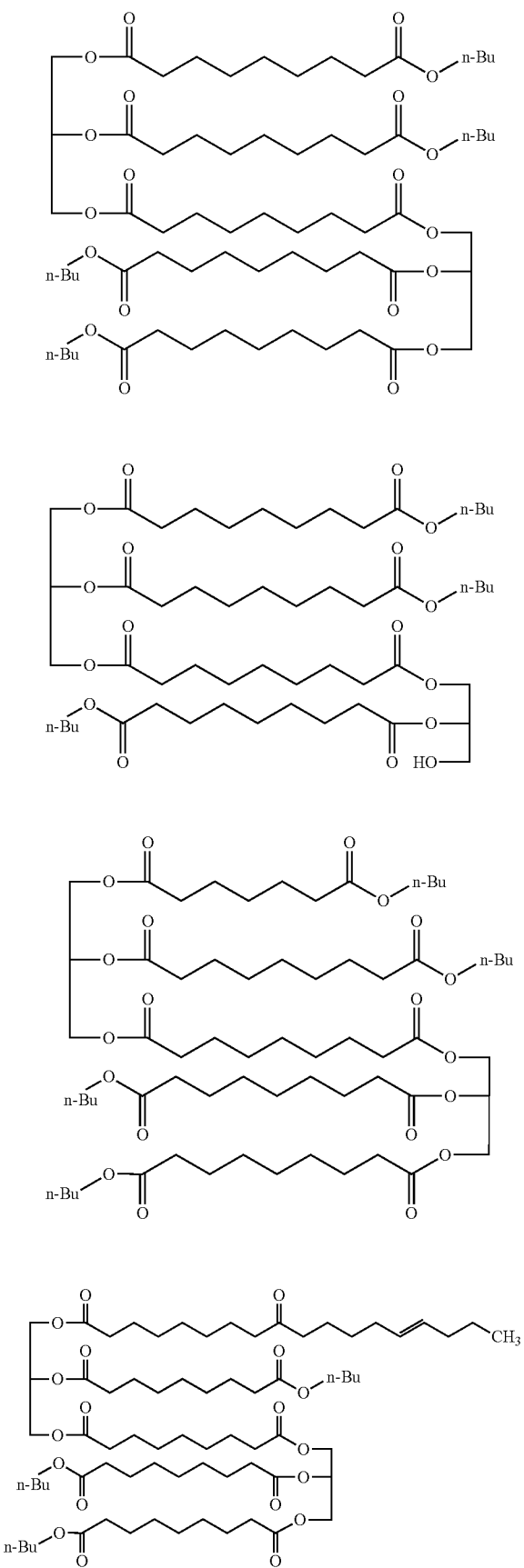

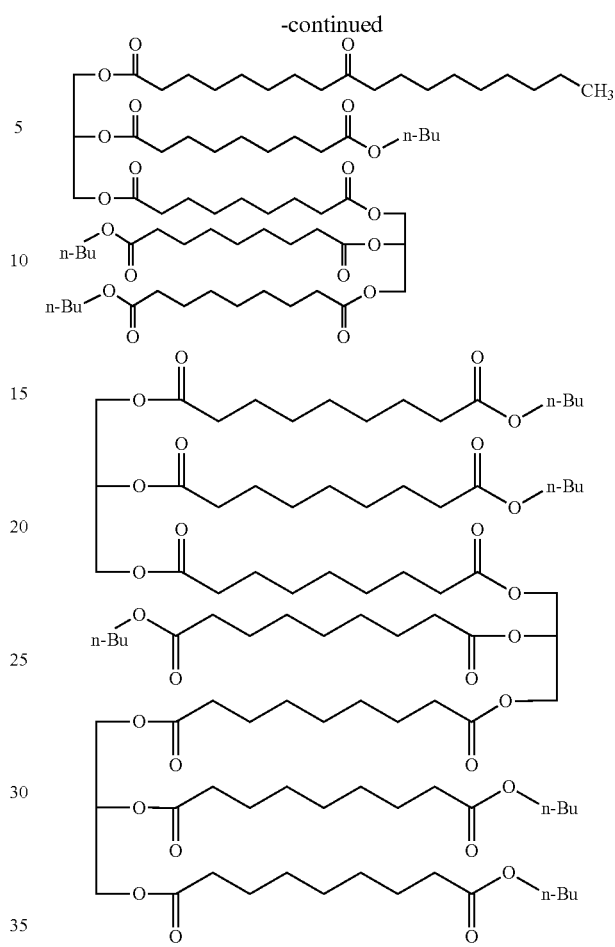

Other examples of oligomeric structures have $R_1=C_7$ alkylene, $R_4=C_4$ alkyl and n=2 and $R_2$ and $R_3$ independently selected from the following groups:

—C(O)—(CH$_2$)$_{6-10}$—COOBu
—C(O)—(CH$_2$)$_{16}$—COOBu
—C(O)—(CH$_2$)$_{6-10}$—CH$_3$
—C(O)—(CH$_2$)$_{16}$—CH$_3$
—C(O)—(CH$_2$)$_{8-9}$—CO—(CH$_2$)$_{7-8}$—CH$_3$
—C(O)—(CH$_2$)$_6$—CO—(CH$_2$)$_7$—CH=CH—CH$_3$.

The mixture of triglycerides according to the present invention may possibly contain monomeric triglycerides containing at least one $C_6$-$C_{24}$ dicarboxylic acid residue. Monomeric triglycerides containing two $C_6$-$C_{24}$ dicarboxylic acids residues, said dicarboxylic acids being the same or different, are particularly preferred. Also preferred are monomeric triglycerides containing at least a $C_6$-$C_{24}$ dicarboxylic acids residue and at least a $C_6$-$C_{24}$ monocarboxylic acids residue having at least a keto group and/or at least an hydroxyl group.

Preferably, the mixture of triglycerides of the present invention further contains oligoglycerols such as diglycerol and triglycerol and their esters with mono- or dicarboxylic acids. Preferred are esters of diglycerols and triglycerols comprising one or more $C_6$-$C_{24}$ dicarboxylic acids. Also preferred are esters of diglycerols and triglycerols comprising at least a saturated or unsaturated monocarboxylic acid containing one or more hydroxyl group and/or a keto group.

The mixture of triglycerides according to this invention can be prepared starting from a mixture of one or more triglycerides containing saturated carboxylic acids having more than one acid function through esterification reactions in presence of alcohols. Short chain alcohols such as for example methyl alcohol, ethyl alcohol, propyl alcohol and butyl alcohol are particularly preferred. Ethyl alcohol and butyl alcohol are particularly advantageous.

Said esterification reactions can be performed with strong acid catalyst. Particularly preferred catalysts are sulphuric acid, paratoluensulfonic acid, methane sulfonic acid and high-temperature resistant strong acid ion exchange resins. The reaction is preferably performed heating the esterification reactor at a temperature of 50-200° C. The reaction is preferably performed removing the water formed in the course of the reaction. The esterification product can be purified to remove the acid catalyst; then the excess alcohol and volatile esters can be separated out, preferably by evaporation under vacuum.

The presence of oligomeric structures according to the invention can be determined with different methods well known to those skilled in the art, such as chromatographic methods combined with mass spectrometry, e.g. LC/MS analysis.

In the preparation of the mixture of triglycerides according to this invention, the starting mixture of one or more triglycerides containing saturated carboxylic acids having more than one acid function may contain free $C_6$-$C_{24}$ monocarboxylic and $C_6$-$C_{24}$ dicarboxylic acids, triglycerides of $C_6$-$C_{24}$ dicarboxylic acids and mono-, di- and triglycerides containing one or more of the following groups consisting of $C_6$-$C_{24}$ dicarboxylic acid residues and $C_6$-$C_{24}$ monocarboxylic acid residues.

A preferred starting mixture of one or more triglycerides containing saturated carboxylic acids having more than one acid function is characterised by a Numerical Average Molecular Weight (Mn) between 200 and 1000 Da, determined by GPC analysis following prior calibration with polystyrene standards.

Preferably, the density of said starting mixture, determined by weighing 100 mL of said mixture at 100° C., is preferably between 0.95 and 1.05 g/cm$^3$.

Preferably, the kinematic viscosity of said starting mixture, calculated as the ratio of dynamic viscosity (measured with a HAAKE VT 500 rotational viscosimeter provided with MV1 rotor at 100° C.) and density, is between 50 and 1500 cSt.

Said starting mixture has preferably an acid number between 50 and 250 mg KOH/g. By acid number is meant the quantity of KOH expressed in mg used to neutralise the acidity of 1 g of substance. The determination is performed according to standard ASTM D974-07 in the presence of phenolphthalein.

The degree of unsaturation of the starting mixture, expressed by the $I_2$ number and determined by titration according to the Wijs method, is preferably between 0 and 150 g $I_2$/100 g.

The saponification number of the starting mixture, understood to be the quantity of KOH expressed in mg consumed in the saponification of 1 gram of substance, is preferably between 100 and 450 mg KOH/g. It is determined by titration with HCl, in the presence of phenolphthalein, of the residual KOH after reflux saponification for 60 minutes.

The hydroxyl number of the starting mixture is preferably between 10 and 100 mg KOH/g. It is the quantity of potassium hydroxide equivalent to the acetylable hydroxyls in 1 gram of substance, and it is understood to be determined according to standard ASTM D 1957-86.

In a preferred embodiment, the starting mixture of one or more triglycerides containing saturated carboxylic acids having more than one acid function is the product of the oxidative cleavage of vegetable oils, effected batchwise or continuously. By way of example, the triglycerides mixtures obtained according to the processes described in patent applications WO2008/138892 and MI2009A002360 are considered. Glycerides mixtures obtained from oxidation of sunflower oil and in particular sunflower oil having a high oleic acid content (HOSO) are of particular interest.

In a particularly preferred embodiment, the starting mixture of one or more triglycerides containing saturated carboxylic acids having more than one acid function is prepared from the organic phase obtained at the end of step d) (i.e. hydrolysis reaction) of the continuous oxidative cleavage process as described in the patent application MI2009A002360. Said organic phase is advantageously evaporated in a thin film evaporator operating at low pressure, preferably at a pressure below 20 mbar, more preferably at a pressure below 10 mbar, with a temperature of diatermic oil 180-300° C., preferably 200-290° C., more preferably 240-280° C., to separate free carboxylic acids from the reaction residue. Preferably, the temperature of the feeding is between 80 and 120° C., more preferably between 100 and 110° C. The temperature of the vapour phase is preferably between 180 and 220° C. more preferably between 200 and 210° C. The temperature of the reaction residue is preferably between 210 and 250° C.

In this case the esterification reaction is then preferably performed with sulphuric acid at a temperature of 70-180° C.

The mixture of triglycerides according to this invention preferably shows a kinematic viscosity at 100° C. between 5 and 400 cSt, determined as described above. Advantageously, the mixture of triglycerides according to this invention preferably shows and a Tg between −85° C. and −40° C., more preferably between −80° C. and −50° C. and even more preferably between −78° C. and −60° C.

Tg is determined by Differential Scanning calorimetry with a single run starting from −100° C. up to 30° C. at a temperature speed of 20° C./min.

The mixture of triglycerides according to the invention preferably have a density between 0.90 and 1.05 g/cm$^3$ (T=100° C.).

Advantageously, the acid number of the product is below 50, preferably below 10 and more preferably below 5 mg KOH/g.

According to a preferred embodiment, the triglycerides mixture have a $I_2$ number between 0 and 140 g $I_2$/100 g.

The saponification number of the triglycerides mixture is preferably between 150 and 500 mg KOH/g.

The hydroxyl number is of the triglycerides mixture still preferably between 10 and 100 mg KOH/g.

The triglycerides mixture according to the present invention are insoluble in boiling water. Said mixture is however completely soluble in diethylether, ethyl alcohol, acetone and chloroform at ambient temperature. It is also characterised by high stability to hydrolysis.

The mixture of triglycerides according to this invention can be used as extender oils in elastomer compositions.

The mixture of triglycerides according to this invention can also be used as component in polyurethane formulations. Other examples of use of the mixture of triglycerides according to this invention are as component in thermoplastic and thermosetting polymers, and in particular in low crystallinity resins for adhesives, hot melts and coatings.

It is also characterised by very high stability to hydrolysis and a low pour point. It therefore can be used as special lubricants. Thanks to the high stability to hydrolysis and a low pour point it can also be used as additive for rubbers, in particular as plasticiser. A further possible use of the mixture of triglycerides according to this invention is as base for inks.

The mixture of triglycerides according to this invention may be used as such or mixed with other compounds according to their end use. In particular they may be mixed with:
a. triglycerides of one or more long-chain carboxylic acids in which at least one of the said carboxylic acids contains adjacent hydroxyl groups,
b. esters other than triglycerides of monocarboxylic and dicarboxylic acids with a polyol.

In a particularly preferred embodiment, the mixture of triglycerides comprising oligomer structures according to this invention may be used as extender oils for elastomer compositions based on natural rubbers (NR), synthetic rubbers or their mixtures. Examples of synthetic rubbers are diene-based rubbers such as styrene-butadiene copolymers (SBR, Styrene-Butadiene Rubber), ethylene-propylene copolymers, in particular ethylene/propylene/diene terpolymers (EPDM, Ethylene/Propylene/Diene Monomer), and thermoplastic elastomers such as styrene-butadiene-styrene (SBS) block copolymers, polar nitrile and styrene-isoprene-styrene (SIS) polar rubbers. The use of elastomer compositions based on natural rubbers or styrene-butadiene rubbers is particularly advantageous.

If used as an extender oil the mixture of triglycerides comprising oligomeric structures according to the invention are used as such or in a mixture with mineral and/or natural oils. Examples of mineral oils are DAE, TDAE and MES; examples of natural oils are oils of animal and plant origin including: peanut oil, Brassicaceae oils, hemp oils, safflower oils, coconut oils, sunflower oils with a various oleic content, jatropha oils, linseed oils, olive oils, macadamia oils, mahua oils, neem oils, palm oils, poppy oils, pongamia oils, castor oils, rice oils, rubber tree seed oils (*Hevea brasiliensis*), maize seed oils, mustard oils, sesame oils and grape seed oils.

The resulting elastomer compositions may also contain vulcanisers (e.g. sulphur) and vulcanisation accelerators, activators and retardants, organic acids, antioxidants, fillers, process coadjuvants and other additives, as known in the art.

These elastomer compositions containing complex oligomeric structures which can be derived from the vegetable oils to which this invention relates are used in particular in the production of tyres.

The mixture of triglycerides comprising oligomeric structures according to the invention will now be described using non-limiting examples.

EXAMPLES

Example 1

A mixture of triglycerides containing saturated carboxylic acids having more than one acid function was obtained from the organic phase after the hydrolysis step d) at the end of the sunflower oil oxidative cleavage process described in the patent application MI2009A002360.

The free carboxylic acids contained in the organic phase were evaporated in a thin film evaporator operating at a pressure of 5 mbar, with a temperature of diathermic oil of 270° C. and with the following operative conditions:
Temperature of the feeding=105° C.
Temperature of the vapour phase=205° C.
Temperature of the reaction residue=250° C.

Figure 1:
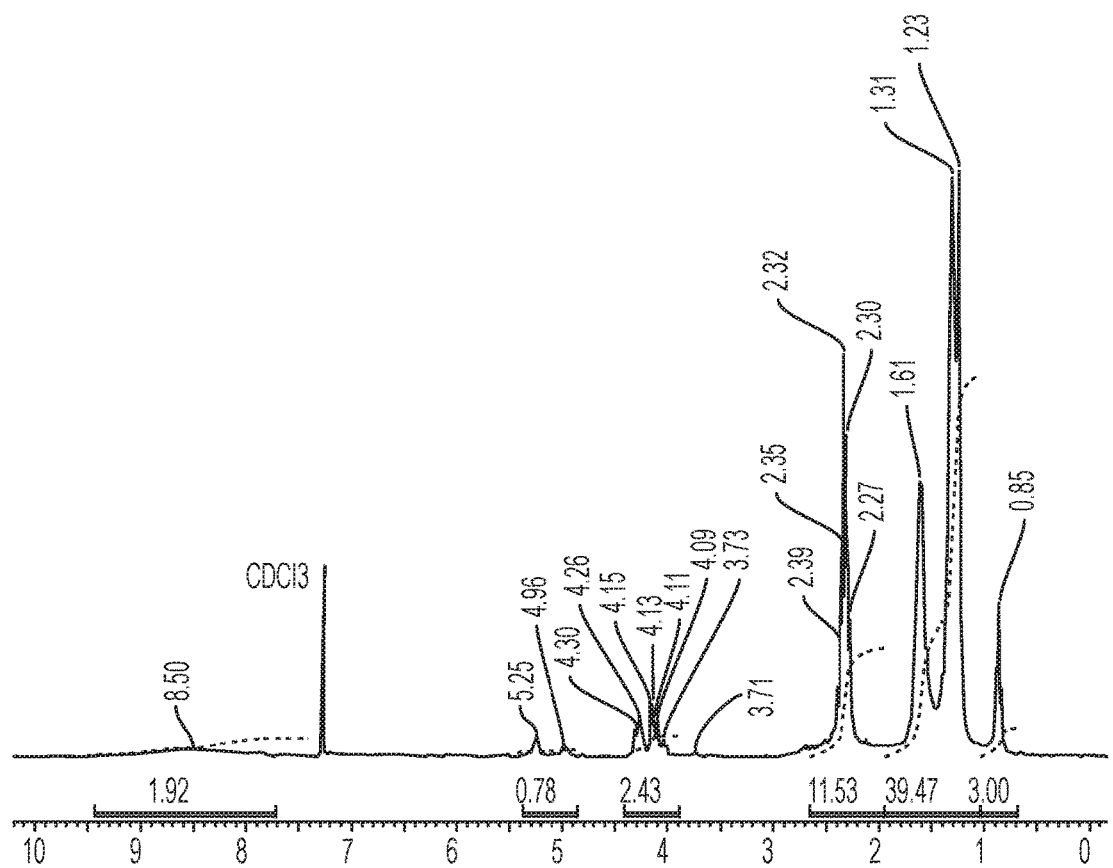
FIG. 1 shows the H-NMR spectrum of the mixture of triglycerides containing saturated carboxylic acids having more than one acid function of Example 1.
Figure 2:
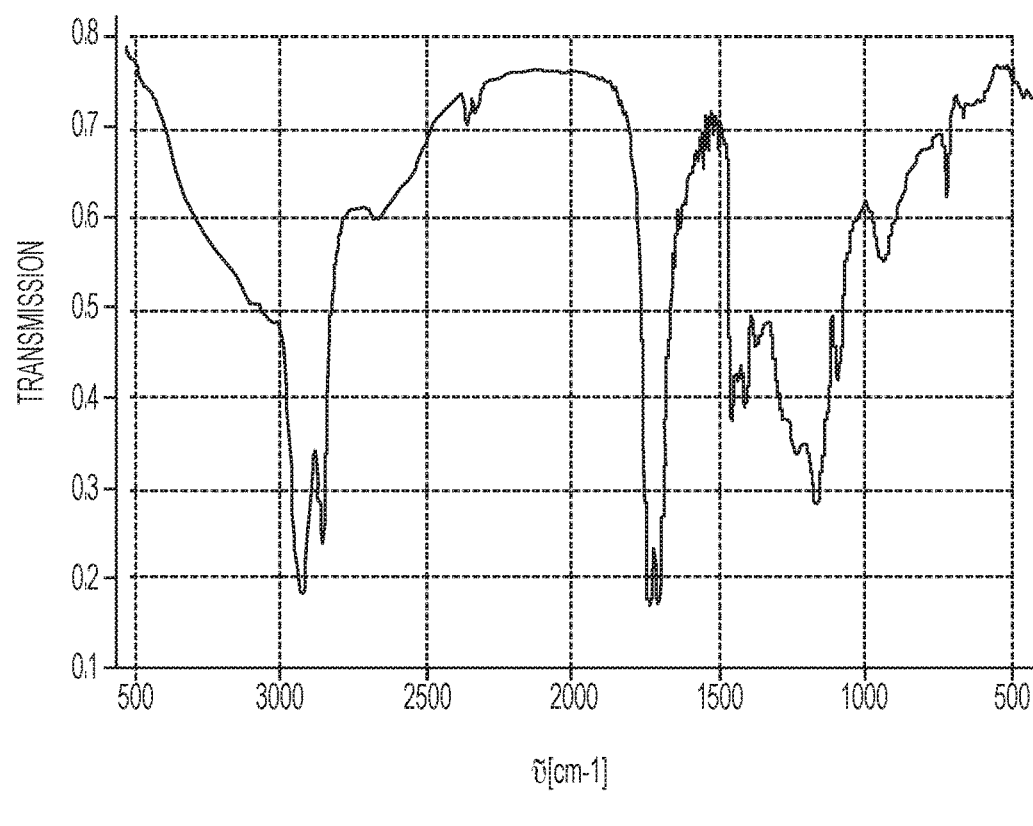
FIG. 2 shows the FT-IR spectrum of the mixture of triglycerides containing saturated carboxylic acids having more than one acid function of Example 1.

FIG. 1 shows the H-NMR spectrum of this mixture of triglycerides, while FIG. 2 shows its FT-IR spectrum. The Mn of the mixture was 215 Da.

Said mixture of triglycerides containing saturated carboxylic acids having more than one acid function was esterified with butyl alcohol and then characterized. The esterification reaction with butyl alcohol, catalysed by sulphuric acid, was performed heating the reaction to reflux and removing the water formed in the course of the reaction by azeotropic distillation. The product was purified by washings with distilled water and aqueous sodium bicarbonate solution to remove the acid catalyst; the excess butyl alcohol and volatile butyl esters were then separated out by evaporation under vacuum (pressure=0.1 mbar, temperature of vapours between 80-190° C.).

The resulting triglyceride mixture was analyzed trough LC/MS/ESI in order to detect the presence of oligomeric structures according to the invention.

The triglyceride mixture was dissolved in a 5:1 mixture of ethyl acetate: acetonitrile and then diluted in methanol to a final concentration of 0.5 mg/ml. The analysis was performed with a LCQ Fleet spectrometer (Thermo Scientific) operating in the following operative conditions:
Ionization: positive ($[M+Na]^+$)
mode: flow injection analysis (FIA);
scan: 100-2000 Da;
API Source: ESI
Sheat Gas Flow rate: 0
Aux Gas Flow rate: 0
Sweep Gas Flow Rate: 0
Capillary Voltage: 2V
Capillary Temp: 275° C.
Tube Lens Voltage: 115V The analysis showed the presence of the following dimer and trimer oligomeric structures, which were identified by their main positive ionization peaks.

| Oligomeric structure | Main positive ionization peaks (m/z) |
|---|---|
| 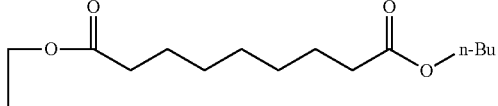 | 1263.3 |
| 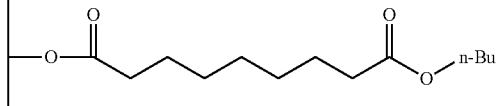 | 1734.3 |

The Mn of the triglycerides mixture containing oligomeric structures according to the invention, as obtained after esterification, was 1950 Da.

Figure 3:
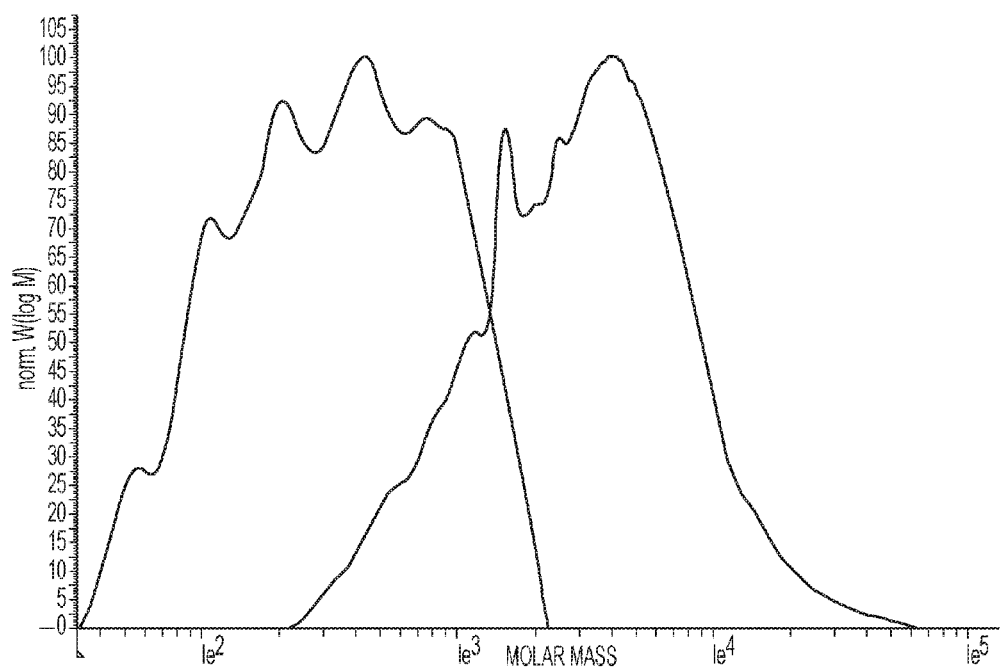
FIG. 3 shows the overlay of the molecular weight distribution of the mixture of triglycerides containing saturated carboxylic acids having more than one acid function before esterification with butyl alcohol with the molecular weight distribution of the triglycerides mixture comprising oligomeric structures according to the Example 1.

FIG. 3 shows the Molecular weight distribution graphs overlay of the glycerides mixture before the esterification reaction with butyl alcohol and of the triglycerides mixture comprising oligomeric structures according to the invention.

Molecular weights were determined by gel permeation chromatography (GPC), using a Agilent 1100 liquid chromatography instrument equipped with three PL gel 5-μm columns serially connected with porosities of 10E4, 10E3 and 500 Angstrom (Å). Chloroform was used as eluent at flow rate of 1 mL/min. The calibration plot was constructed with polystyrene standards. Column temperature was set to be 40° C. Samples were dissolved in chloroform (0.15 mg/ml) and filtered with a Teflon filter (pore size: 0.20 μm).

Physical and chemical properties of the resulting mixture of oligomeric triglycerides esterified with butyl alcohol are shown in Table 1.

Examples 2-4

The same mixture of triglycerides containing saturated carboxylic acids having more than one acid function in Example 1 was esterified with ethyl alcohol.

The esterification reaction with ethyl alcohol, catalysed by sulphuric acid, was performed in toluene heating the reaction to reflux and removing the water formed in the course of the reaction by azeotropic distillation The ester was purified by dilution with ether and successive washings with distilled water and aqueous sodium bicarbonate solution to remove the acid catalyst; the excess ethanol and volatile ethyl esters were then separated out by evaporation under vacuum (pressure=0.1 mbar, temperature of vapours between 60-160° C.).

The chemical and physical properties of the resulting mixture of triglycerides esterified with ethanol (Example 2) are shown in Table 1 and compared to the properties of the same starting mixture esterified with butanol (Example 1) and to the properties of a raw vegetable oil (HOSO, High Oleic Sunflower Oil, used in Comparative Example 4).

TABLE 1

Physical and chemical properties of the esterified mixture of triglycerides of Example 1 (butyl ester) and of Example 2 (ethyl ester) compared to a vegetable oil (High Oleic Sunflower Oil).

| Physical and chemical properties | Example 1 | Example 2 | HOSO |
|---|---|---|---|
| Glass Transition Temperature (° C.) | −71 | −48 | −91.5 |
| Density at 100° C. (g/cm$^3$) | 0.96 | 0.94 | 0.88 |
| Specific gravity at 100° C. (N/m$^3$) | 9408 | 9212 | 8624 |
| Dynamic viscosity at 100° C. (cP) | 30.2 | 14.7 | 14.3 |
| Kinematic viscosity at 100° C. (cSt) | 31.5 | 15.7 | 16.25 |
| Acid number (mg KOH/g) | 3.2 | 4.8 | 0.23 |
| Saponification number (mg KOH/g) | 256.2 | 268.3 | 188 |
| Iodine number (mg I$_2$/100 g) | 52.2 | 47.9 | 82 |
| Hydroxyl number (mg KOH/g) | 35.2 | 48.3 | <1 |

The obtained mixture was used in extender oil in an elastomer composition (Example 2). The resulting elastomer composition was compared with similar elastomer compositions containing a commonly used mineral oil (TDAE, Example 3) and a vegetable oil as such (high oleic sunflower oil, HOSO, Example 4) as extender oils.

The extender oil used in comparison Example 3 is a mineral oil of the TDAE type (treated distillate aromatic extracts, aromatic oils treated to reduce the polycyclic aromatics content) approved as an extender oil for elastomer compositions for tyres.

The extender oil used in comparison Example 4 is an HOSO sunflower oil (High Oleic Sunflower Oil) containing 82% of oleic acid, 10% of linoleic acid, 4.5% of palmitic acid and 3.5% of stearic acid.

Three identical elastomer compositions containing SBR as the base elastomer were then prepared. These compositions differed only in the compound used as the extender oil.

Table 2 shows the quantities by weight in the elastomer compositions, specifying the quantities of the individual ingredients in relation to one hundred parts of rubber (phr).

TABLE 2

Elastomer composition

| Material | phr |
|---|---|
| SBR 1502 | 100.0 |
| Precipitated silica (Zeosil 1165 MP) | 60.0 |
| Extender oil | 17.0 |
| Silane (TESPT) | 4.8 |
| Preservative (TMQ) | 1.5 |
| Activator (ZnO) | 2.6 |
| Vulcanisers (sulphur, MBTS, TBBS) | 3.8 |

The components were dispersed in the rubber using a Banbury Pomini-Farrel model PL04 mixer. After filler had been added to the rubber a mastication stage of 30 sec at a temperature of 125° C. was initiated, at a rate of 60 rpm.

⅓ of the silica and ⅓ of the extender oil were first added, allowing them to mix for 30 secs, then ⅓ of silica, ⅓ of oil and the silane were added, mixing for a further 30 secs. The remainder of the silica, oil and preservative were then successively added to the mixer, mixing for a further 30 sec.

Mixing then continued for a maximum time of 7 minutes, stopping the process in any event at 160° C.

The mixture was discharged, cooled and reloaded into the mixer at a temperature of 140° C., mixing continuing at 60 rpm for a maximum time of 10 minutes, stopping the process in any event at 160° C.

The mixture was discharged and allowed to cool, and then reloaded into the mixer at 55° C. The activator and vulcanisers were added, and allowed to mix for 2 minutes at 60 rpm.

The mixtures so obtained were vulcanised in a press at 160° C. for 10 minutes, to prepare test specimens intended for mechanical characterization.

The elastomer compositions in Examples 2-4 were then compared on the basis of tensile tests, measuring the Ultimate Tensile Strenght ($\sigma_b$), Elongation at Break ($\epsilon_b$) and Elastic Modulus with reference to an elongation of 200% ($E_{200\%}$) according to standard ASTM D412. Rebound was then tested according to standard ASTM D7121 and Shore A Hardness according to standard ASTM D2240.

As may be seen from the data shown in Table 3, all the elastomer compositions show substantially comparable Rebound and Shore Hardness properties. The elastomer composition containing the mixture of triglycerides comprising the oligomeric structure according to the invention (Example 2) as extender oil shows better Ultimate Tensile Strength and Elastic Modulus than the comparison compositions containing TDAE and HOSO (Examples 3 and 4).

TABLE 3

Mechanical properties of the elastomer compositions

| Examples | $\sigma_b$ (MPa) | $\epsilon_b$ (%) | $E_{(200\%)}$ (MPa) | Rebound resilience (%) | Shore A |
|---|---|---|---|---|---|
| 2 | 12.2 | 374 | 2.7 | 36.2 | 38 |
| Comparison-3 | 8.0 | 388 | 1.7 | 36.1 | 43 |
| Comparison-4 | 10.5 | 433 | 1.5 | 36.0 | 30 |

The data provided indicate a better degree of vulcanisation in the compositions containing the mixture of triglycerides according to the invention. Its use as an extender oil therefore has the advantage of improved compatibility with the rubber in comparison with conventional extender oils and improved tensile properties without an adverse effect on other properties.

The invention claimed is:

1. A method for producing an ink composition which comprises adding a mixture of triglycerides obtained from vegetable oils comprising one or more of the following oligomeric structures:

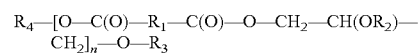

wherein
R$_1$ is selected from C$_2$-C$_{22}$ alkylenes,
R$_2$ is selected from one or more of the following groups consisting of C$_6$-C$_{24}$ dicarboxylic acid residues and C$_6$-C$_{24}$ monocarboxylic acid residues,
R$_3$ is selected from one or more of the following groups consisting of H, C$_6$-C$_{24}$ dicarboxylic acid residues and C$_6$-C$_{24}$ monocarboxylic acid residues,
R$_4$ is an alkyl group,
n is an integer greater than or equal to 2, said $C_6$-$C_{24}$ dicarboxylic acid residues of R2 and R3 being esterified with monoalcohols and said mixture of triglycerides having a Numerical Average Molecular Weight (Mn) of between 800 and 10.000 Da to an ink composition.

2. A method according to claim 1 wherein R1 of the said oligomeric structures is a $C_6$-$C_{11}$ alkylene.

3. A method according to claim 1, wherein the $C_6$-$C_{24}$ dicarboxylic acid residues of $R_2$ and $R_3$ are esterified with linear or branched $C_1$-$C_{12}$ monoalcohols.

4. A method according to claim 1 wherein said monoalcohols are methyl alcohol, ethyl alcohol, propyl alcohol and butyl alcohol.

5. A method according to claim 1, wherein $R_4$ is a branched or linear $C_1$-$C_{12}$ alkyl group.

6. A method according to claim 1, wherein the $C_6$-$C_{24}$ dicarboxylic acid residues of $R_2$ and $R_3$ are suberic acid, azelaic acid, brassylic acid and their mixtures.

7. A method according to claim 1, wherein "n" is an integer equal to 2 or equal to 3.

8. A method according to claim 1, wherein the said mixture of triglycerides contains monomeric triglycerides containing at least one $C_6$-$C_{24}$ dicarboxylic acid residue.

9. A method according to claim 1, wherein the said mixture of triglycerides shows a kinematic viscosity at 100° C. between 5 and 400 cSt.

10. A method according to claim 1, wherein the said mixture of triglycerides shows a Tg between −85° C. and −40° C.

11. A method according to claim 1, wherein the said mixture of triglycerides shows a density between 0.90 and 1.05 g/cm$^3$.

12. A method according to claim 1, wherein the said mixture of triglycerides shows an acid number below 50 mg KOH/g.

13. A method according to claim 1, wherein the said mixture of triglycerides shows a $I_2$ number between 0 and 140 g $I_2$/100 g.

14. A method according to claim 1, wherein the said mixture of triglycerides shows a saponification number between 150 and 500 mg KOH/g.

15. A method according to claim 1, wherein the said mixture of triglycerides shows an hydroxyl number between 10 and 100 mg KOH/g.

16. A method according to claim 1, wherein the said mixture of triglycerides is added as ink base.

* * * * *